US008062739B2

(12) United States Patent
Liu et al.

(10) Patent No.: US 8,062,739 B2
(45) Date of Patent: Nov. 22, 2011

(54) HYDROGELS WITH GRADIENT

(75) Inventors: Kaifeng Liu, Notre Dame, IN (US);
Brian Thomas, Columbia City, IN (US);
Steven Charlebois, Goshen, IN (US)

(73) Assignee: Zimmer, Inc., Warsaw, IN (US)

( * ) Notice: Subject to any disclaimer, the term of this patent is extended or adjusted under 35 U.S.C. 154(b) by 1117 days.

(21) Appl. No.: 11/848,698

(22) Filed: Aug. 31, 2007

(65) Prior Publication Data
US 2009/0062408 A1 Mar. 5, 2009

(51) Int. Cl.
*B32B 7/02* (2006.01)
*H05B 6/00* (2006.01)
(52) U.S. Cl. ........................ 428/212; 264/478
(58) Field of Classification Search .................. None
See application file for complete search history.

(56) References Cited

U.S. PATENT DOCUMENTS

| | | |
|---|---|---|
| 3,200,178 A | 8/1965 | Kanji |
| 3,862,265 A | 1/1975 | Steinkamp |
| 3,875,302 A | 4/1975 | Inoue |
| 4,036,788 A | 7/1977 | Steckler |
| 4,058,491 A | 11/1977 | Steckler |
| 4,060,678 A | 11/1977 | Steckler |
| 4,071,508 A | 1/1978 | Steckler |
| 4,279,795 A | 7/1981 | Yamashita |
| 4,300,820 A | 11/1981 | Shah |
| 4,379,874 A | 4/1983 | Stoy |
| 4,451,599 A | 5/1984 | Odorzynski |
| 4,451,630 A | 5/1984 | Atkinson |
| 4,464,438 A | 8/1984 | Lu |
| 4,472,542 A | 9/1984 | Nambu |
| 4,521,568 A * | 6/1985 | Mori et al. .................... 525/309 |
| 4,640,941 A | 2/1987 | Park |
| 4,656,216 A | 4/1987 | Muller |
| 4,663,358 A | 5/1987 | Hyon |
| 4,664,857 A | 5/1987 | Nambu |
| 4,699,146 A | 10/1987 | Sieverding |
| 4,734,097 A | 3/1988 | Tanabe |
| 4,771,089 A | 9/1988 | Ofstead |
| 4,772,287 A | 9/1988 | Ray |
| 4,808,353 A | 2/1989 | Nambu |
| 4,842,597 A | 6/1989 | Brook |
| 4,851,168 A | 7/1989 | Graiver |
| 4,859,719 A | 8/1989 | Ofstead |
| 4,871,490 A | 10/1989 | Rosiak |
| 4,874,562 A | 10/1989 | Hyon |
| 4,875,562 A | 10/1989 | Hyon |
| 4,915,974 A | 4/1990 | D'Amelia |
| 4,956,122 A | 9/1990 | Payne |
| 4,966,924 A | 10/1990 | Hyon |
| 4,988,761 A | 1/1991 | Ikada |
| 5,028,648 A | 7/1991 | Famili |
| 5,047,055 A | 9/1991 | Bao |
| 5,053,455 A | 10/1991 | Kroggel |
| 5,106,876 A | 4/1992 | Kawamura |
| 5,118,779 A | 6/1992 | Szycher |
| 5,122,565 A | 6/1992 | George |
| 5,157,093 A | 10/1992 | Harisiades |
| 5,189,097 A | 2/1993 | LaFleur |
| 5,192,326 A | 3/1993 | Bao |
| 5,244,799 A | 9/1993 | Anderson |
| 5,276,079 A | 1/1994 | Duan et al. |
| 5,288,503 A | 2/1994 | Wood |
| 5,306,311 A | 4/1994 | Stone |
| 5,311,223 A | 5/1994 | Vanderlaan |
| 5,315,478 A | 5/1994 | Cadwell |
| 5,334,634 A | 8/1994 | Bastiolo |
| 5,336,551 A | 8/1994 | Graiver |
| 5,358,525 A | 10/1994 | Fox |
| 5,360,830 A | 11/1994 | Bastiolo |
| 5,362,803 A | 11/1994 | LaFleur |
| 5,364,547 A | 11/1994 | Babb et al. |
| 5,407,055 A | 4/1995 | Tanaka |
| 5,409,966 A | 4/1995 | Duan et al. |
| 5,410,016 A | 4/1995 | Hubbell |
| 5,458,643 A | 10/1995 | Oka |
| 5,527,271 A | 6/1996 | Shah |
| 5,540,033 A | 7/1996 | Fox |
| 5,552,096 A | 9/1996 | Auda |
| 5,576,072 A | 11/1996 | Hostettler |
| 5,580,938 A | 12/1996 | Gutweiller |
| 5,624,463 A | 4/1997 | Stone |
| 5,632,774 A | 5/1997 | Babian |
| 5,674,295 A | 10/1997 | Ray |
| 5,681,300 A | 10/1997 | Ahr |
| 5,705,296 A | 1/1998 | Kamauchi |
| 5,709,854 A | 1/1998 | Griffith-Cima |
| 5,711,960 A | 1/1998 | Shikinami |

(Continued)

FOREIGN PATENT DOCUMENTS

EP 0256293 2/1988

(Continued)

OTHER PUBLICATIONS

EP Search Report for EP06255568.5, Jun. 15, 2007.
Rao et al. J. Chem. Soc. Dalton Trans., 1939-1944.
Li et al. Anal. Biochem., 256, 130-132 (1998).
Anseth et al. "In situ forming degradable networks and their application in tissue engineering and drug delivery." J. Controlled Release 78 (2002), 199-209, 2002.
Lin-Gibson et al. "Synthesis and Characterization of PEG Dimethacrylates and Their Hydrogels." Biomacromolecules 2004, 5, 1280-1287, 2004.
Peppas et al. Structure and Applications of Poly(vinyl alcohol) Hydrogels Produced by Conventional Crosslinking or b Freezing/Thawing Methods. Adv. Polymer Sci. 153, 37 (2000).
LeGeros R. Z., "Calcium phosphates in oral biology and medicine," Monograph in Oral Science, vol. 15, pp. 1-201.
Chow et al.,"Octacalcium Phosphate," Monograph in Oral Science, vol. 18, pp. 94-112 and 130-148.

(Continued)

*Primary Examiner* — Sheeba Ahmed
(74) *Attorney, Agent, or Firm* — Cook Alex Ltd.

(57) ABSTRACT

The present invention provides a hydrogel article having a multi-layered structure and exhibiting a gradient in polymer molecular weight. The invention also provides a method of forming a hydrogel article having a multi-layered structure and exhibiting a gradient in polymer molecular weight.

12 Claims, 2 Drawing Sheets

U.S. PATENT DOCUMENTS

| | | | |
|---|---|---|---|
| 5,716,404 A | 2/1998 | Vacanti | |
| 5,723,311 A | 3/1998 | Tubo et al. | |
| 5,723,331 A | 3/1998 | Tubo | |
| 5,834,029 A | 11/1998 | Bellamkonda | |
| 5,879,713 A | 3/1999 | Roth et al. | |
| 5,891,826 A | 4/1999 | Tsaur et al. | |
| 5,941,909 A | 8/1999 | Purkait | |
| 5,976,186 A | 11/1999 | Bao | |
| 5,981,826 A | 11/1999 | Ku | |
| 6,001,395 A * | 12/1999 | Coombes et al. | 424/501 |
| 6,015,576 A | 1/2000 | See | |
| 6,017,577 A | 1/2000 | Hostettler | |
| 6,040,493 A | 3/2000 | Cooke | |
| 6,080,488 A | 6/2000 | Hostettler | |
| 6,117,449 A | 9/2000 | See | |
| 6,120,904 A | 9/2000 | Hostettler | |
| 6,121,341 A | 9/2000 | Sawhney | |
| 6,129,761 A | 10/2000 | Hubbell | |
| 6,132,468 A | 10/2000 | Mansmann | |
| 6,139,963 A | 10/2000 | Fujii | |
| 6,146,686 A | 11/2000 | Leitao | |
| 6,156,345 A | 12/2000 | Chudzik | |
| 6,156,572 A | 12/2000 | Bettamkonda | |
| 6,162,456 A | 12/2000 | Dunbar | |
| 6,180,132 B1 | 1/2001 | Huang | |
| 6,180,606 B1 | 1/2001 | Chen | |
| 6,184,197 B1 | 2/2001 | Heinzman | |
| 6,187,048 B1 | 2/2001 | Mitner | |
| 6,207,185 B1 | 3/2001 | See | |
| 6,211,296 B1 | 4/2001 | Frate | |
| 6,224,893 B1 | 5/2001 | Langer | |
| 6,231,605 B1 | 5/2001 | Ku | |
| 6,232,406 B1 | 5/2001 | Stoy | |
| 6,238,691 B1 | 5/2001 | Huang | |
| 6,268,405 B1 | 7/2001 | Yao | |
| 6,271,278 B1 | 8/2001 | Park | |
| 6,280,475 B1 | 8/2001 | Bao | |
| 6,306,424 B1 | 10/2001 | Vyakamam | |
| 6,365,149 B2 | 4/2002 | Vyakamam | |
| 6,371,984 B1 | 4/2002 | Van Dyke | |
| 6,372,283 B1 | 4/2002 | Shim | |
| 6,375,634 B1 | 4/2002 | Carroll | |
| 6,387,325 B1 | 5/2002 | Keusch | |
| 6,402,784 B1 | 6/2002 | Wardlaw | |
| 6,443,988 B2 | 9/2002 | Felt | |
| 6,509,098 B1 | 1/2003 | Merrill | |
| 6,531,147 B2 | 3/2003 | Sawhney | |
| 6,533,817 B1 | 3/2003 | Norton | |
| 6,583,219 B2 | 6/2003 | Won | |
| 6,602,952 B1 | 8/2003 | Bentley | |
| 6,608,117 B1 | 8/2003 | Gvozdic | |
| 6,620,196 B1 | 9/2003 | Trieu | |
| 6,626,945 B2 | 9/2003 | Simon | |
| 6,629,997 B2 | 10/2003 | Mansmann | |
| 6,630,457 B1 | 10/2003 | Aeschlimann et al. | |
| 6,632,246 B1 | 10/2003 | Simon | |
| 6,645,517 B2 | 11/2003 | West | |
| 6,692,738 B2 | 2/2004 | MacLaughlin | |
| 6,706,690 B2 | 3/2004 | Reich | |
| 6,709,668 B2 | 3/2004 | Won | |
| 6,710,104 B2 | 3/2004 | Haraguchi | |
| 6,710,126 B1 | 3/2004 | Hirt | |
| 6,723,781 B1 | 4/2004 | Frate | |
| 6,730,298 B2 | 5/2004 | Griffith-Cima | |
| 6,733,533 B1 | 5/2004 | Lozier | |
| 6,780,840 B1 | 8/2004 | DeVore | |
| 6,783,546 B2 | 8/2004 | Zucherman | |
| 6,783,721 B2 | 8/2004 | Higham | |
| 6,803,420 B2 | 10/2004 | Cleary | |
| 6,852,772 B2 | 2/2005 | Muratoglu | |
| 6,855,743 B1 | 2/2005 | Gvodzic | |
| 6,861,067 B2 | 3/2005 | McGhee | |
| 7,235,592 B2 | 6/2007 | Muratoglu | |
| 7,531,000 B2 | 5/2009 | Hodorek | |
| 2001/0026810 A1 | 10/2001 | McGhee | |
| 2001/0032019 A1 | 10/2001 | Van Dyke | |
| 2001/0049417 A1 | 12/2001 | Frate | |
| 2001/0053897 A1 | 12/2001 | Frate et al. | |
| 2001/0053987 A1 | 12/2001 | Frate | |
| 2002/0022884 A1 | 2/2002 | Mansmann | |
| 2002/0026244 A1 | 2/2002 | Trieu | |
| 2002/0029083 A1 | 3/2002 | Zucherman | |
| 2002/0049498 A1 | 4/2002 | Yuksel | |
| 2002/0131952 A1 | 9/2002 | Hennink | |
| 2002/0151979 A1 | 10/2002 | Lambrecht | |
| 2002/0173855 A1 | 11/2002 | Mansmann | |
| 2002/0193531 A1 | 12/2002 | Stoy | |
| 2003/0008396 A1 | 1/2003 | Ku | |
| 2003/0065389 A1 | 4/2003 | Petersen | |
| 2003/0080465 A1 | 5/2003 | Higham | |
| 2003/0099709 A1 | 5/2003 | Shah | |
| 2003/0104031 A1 * | 6/2003 | Dumont et al. | 424/426 |
| 2003/0130427 A1 | 7/2003 | Cleary | |
| 2003/0152528 A1 | 8/2003 | Singh et al. | |
| 2003/0170308 A1 | 9/2003 | Cleary | |
| 2003/0195628 A1 | 10/2003 | Bao | |
| 2003/0232895 A1 | 12/2003 | Omidian | |
| 2003/0236323 A1 | 12/2003 | Ratner | |
| 2004/0002764 A1 | 1/2004 | Gainor | |
| 2004/0002770 A1 * | 1/2004 | King et al. | 623/23.51 |
| 2004/0005423 A1 | 1/2004 | Dalton | |
| 2004/0030392 A1 | 2/2004 | Lambrecht | |
| 2004/0039447 A1 | 2/2004 | Simon | |
| 2004/0092653 A1 | 5/2004 | Ruberti | |
| 2004/0096509 A1 | 5/2004 | Hutchens | |
| 2004/0116641 A1 | 6/2004 | Mather | |
| 2004/0121951 A1 | 6/2004 | Rhee | |
| 2004/0127618 A1 | 7/2004 | Ulmer | |
| 2004/0127992 A1 | 7/2004 | Sehman | |
| 2004/0131582 A1 | 7/2004 | Grinstaff | |
| 2004/0131852 A1 | 7/2004 | Grinstaff | |
| 2004/0133280 A1 | 7/2004 | Trieu | |
| 2004/0143329 A1 | 7/2004 | Ku | |
| 2004/0147673 A1 | 7/2004 | Calabro | |
| 2004/0153163 A1 | 8/2004 | Posner | |
| 2004/0161444 A1 | 8/2004 | Song | |
| 2004/0171740 A1 | 9/2004 | Ruberti | |
| 2004/0199250 A1 | 10/2004 | Fell | |
| 2004/0220296 A1 | 11/2004 | Lowman | |
| 2004/0242770 A1 | 12/2004 | Feldstein | |
| 2004/0244978 A1 | 12/2004 | Shaarpour | |
| 2005/0004560 A1 | 1/2005 | Cox | |
| 2005/0027069 A1 | 2/2005 | Rhee | |
| 2005/0048103 A1 | 3/2005 | Cleary | |
| 2005/0049365 A1 | 3/2005 | Cleary | |
| 2005/0075454 A1 | 4/2005 | Plochocka et al. | |
| 2005/0095296 A1 | 5/2005 | Lowman | |
| 2005/0107561 A1 | 5/2005 | Lee et al. | |
| 2005/0197441 A1 | 9/2005 | Shibutani | |
| 2006/0078587 A1 | 4/2006 | Leong | |
| 2006/0141002 A1 | 6/2006 | Liu | |
| 2006/0188487 A1 | 8/2006 | Thomas | |
| 2007/0004861 A1 | 1/2007 | Cai | |
| 2007/0202323 A1 | 8/2007 | Kleiner | |
| 2007/0293651 A1 | 12/2007 | Tada | |
| 2008/0090145 A1 | 4/2008 | Hiwara | |
| 2009/0053318 A1 | 2/2009 | Tan | |

FOREIGN PATENT DOCUMENTS

| | | |
|---|---|---|
| EP | 0290616 | 11/1988 |
| EP | 0365108 | 4/1990 |
| EP | 0505634 | 9/1992 |
| EP | 0696210 | 2/1996 |
| EP | 0738762 | 4/1996 |
| EP | 0784987 | 7/1997 |
| EP | 0835143 | 4/1998 |
| EP | 0845480 | 6/1998 |
| EP | 0927053 | 7/1999 |
| EP | 1079224 | 2/2001 |
| EP | 1174463 | 1/2002 |
| EP | 1593400 | 11/2005 |
| EP | 1595899 | 11/2005 |
| FR | 2786400 | 6/2000 |
| FR | 2865939 | 8/2005 |
| FR | 2866571 | 8/2005 |
| GB | 2338958 | 10/2000 |
| JP | 01178545 | 7/1989 |

| | | |
|---|---|---|
| JP | 01305959 | 12/1989 |
| JP | 03141957 | 6/1991 |
| JP | 04303444 | 10/1992 |
| JP | 09124730 | 5/1997 |
| JP | 09124731 | 5/1997 |
| JP | 10036524 | 2/1998 |
| JP | 10036534 | 2/1998 |
| JP | 10043286 | 2/1998 |
| JP | 10306534 | 2/1998 |
| WO | 9015082 A1 | 12/1990 |
| WO | WO 94/13235 | 6/1994 |
| WO | 9417851 | 8/1994 |
| WO | WO9502616 | 1/1995 |
| WO | 9526699 | 10/1995 |
| WO | 9640304 | 4/1998 |
| WO | 9817215 | 4/1998 |
| WO | 9853768 | 12/1998 |
| WO | 9903454 | 1/1999 |
| WO | 9913923 | 3/1999 |
| WO | 9907320 | 12/1999 |
| WO | 9967320 | 12/1999 |
| WO | 0117574 | 3/2001 |
| WO | WO 01/19283 | 3/2001 |
| WO | 0177197 | 10/2001 |
| WO | WO01/77197 | 10/2001 |
| WO | WO 02/04570 | 1/2002 |
| WO | 0213871 | 2/2002 |
| WO | 02060501 | 8/2002 |
| WO | 02087642 | 11/2002 |
| WO | 02087645 | 11/2002 |
| WO | 03008007 | 1/2003 |
| WO | 03074099 | 9/2003 |
| WO | 03092359 | 10/2003 |
| WO | WO 03/082359 | 10/2003 |
| WO | 2004007651 | 1/2004 |
| WO | 2004029174 | 4/2004 |
| WO | 2004031253 | 4/2004 |
| WO | 2004047690 | 6/2004 |
| WO | 2004055057 | 7/2004 |
| WO | 2004060427 | 7/2004 |
| WO | 2004063388 | 7/2004 |
| WO | 2004064693 | 8/2004 |
| WO | 2004066704 | 8/2004 |
| WO | 2004069296 | 8/2004 |
| WO | 2004069296 A1 | 8/2004 |
| WO | 2004072138 | 8/2004 |
| WO | 2004093786 | 11/2004 |
| WO | 2005004943 | 1/2005 |
| WO | WO2005004943 | 1/2005 |
| WO | 2005035726 | 4/2005 |
| WO | WO 2005/030832 | 4/2005 |
| WO | WO2005030382 | 4/2005 |
| WO | 2006021054 | 3/2006 |
| WO | 2006091706 | 8/2006 |
| WO | 2007067697 | 6/2007 |
| WO | 2007015208 | 8/2007 |
| WO | WO 2008/144514 | 11/2008 |
| WO | 2009020793 | 2/2009 |
| WO | WO 2009/032430 | 3/2009 |
| WO | WO 2009/088654 | 7/2009 |

OTHER PUBLICATIONS

Carey et al., Adv. Org. Chem., Part B., p. 892, 2001.
Hassan et al. "Cellular PVA Hydrogels Produced by Freeze/Thawing." J. Appl. Poly. Sci. 76, 2075 (2000).
Moro et. al. "Surface Grafting of Artificial Joints with Biocompatible Polymer for Preventing Periprosthetic Osteolysis." Nature Materials, 3, 829 (2004).
Hickey et al. :Solute Diffusion in Poly(vinyl)alchohol/poly(acrylic acid) composite membranes prepared by freezing/thawing techniques. Polymer 38, pp. 5931-5936 (1997).
Wang B., et al. The Influence of Polymer concentration on the Radiation-chemical Yield of Intermolecular Crosslinking of Poly(Vinyl Alcohol) by gamma-rays in Deoxygenated Aqueous Solution. Radiation Physics and Chemistry, 2000. 59: p. 91-95.
Rosiak, J. M. & Ulanski, P. Synthesis of hydrogels by irradiation of polymers in aqueous solution, Radiation Physics and Chemistry 1999 55: 139-151.
Stammen, J. A., et al. Mechanical properties of a novel PVA hydrogel in shear and unconfined compression Biomaterials, 2001 22: p. 799-806.
Yamaura, K., et al. Properties of gels obtained by freezing/thawing of poly(vinyl alcohol)/water/dimethyl sulfoxide solutions. Journal of Applied Polymer Science 1989 37:2709-2718.
Lozinsky, V. I. and Damshkaln, L. G. Study of cryostructuration of polymer systems. XVIII. Poly(vinyl alcohol) cryogels: Dynamics of cryotropic gel formation. Journal of Applied Polymer Science 2000 77:2017-2023.
Oka M et al. "Development of artificial articular cartilage," Pro. Inst. Mech. Eng. 2000 214:59-68.
EP Search Report for EP 06256525.4 dated May 20, 2007.
ISR/WO for PCT/EP2005/010931 dated Feb. 16, 2006.
ISR/WO for PCT/US2007/064782 dated May 3, 2008.
EP Search Report for EP06256452.1 dated May 23, 2007.
ISR/WO for PCT/US2006/046725 dated Jul. 28, 2008.
Park K.R. et al. "Synthesis of PVA/PVP Hydrogels having Two-Layer by Radiation and their Physical Properties." Rad. Phys. and Chem., Jun. 2003, pp. 361-365. vol. 67, No. 3-4.
Hassan C.M. "Diffusional Characteristics of Freeze/Thawed Poly(vinyl alcohol) hydrogels: Applications to protein controlled release from multilaminate devices." Eur. J. Pharm. and Biopharm., 2000, pp. 161-165, vol. 49.
Bass L.S. "Laser Tissue Welding: A Comprehensive Review of Current and Future Clinical Applications," Lasers in Surgery and Medicine, 1995, pp. 315-349. vol. 17.
Search Report for PCT/US2008/071435 dated Feb. 2, 2009.
Bryant, S.J. et al. "Crosslinking Density Influences Chondrocyte Metabolism in Dynamically Leaded Photocrosslinked Poly(ethylene glycol) Hydrogels." Ann. Biomed. Eng., Mar. 2004, pp. 407-417, vol. 3, No. 3.
Bryant, S.J. et al. "The Effects if Scaffold thickness on Tissue Engineered Cartilage in Photocrosslinked Poly (ethylene oxide) hydrogels." Biomaterials 22, 2001, pp. 619-628.
Bryant, S.J. et al. "Photocrosslinkable Poly(ethylene oxide) and Poly (vinyl alcohol) Hydrogels for Tissue Engineering Cartilage." 21st Annual Conference and the 1999 Annual Fall Meeting of the Biomedical Engineering Society, Oct. 13-15, 1999, Atlanta, GA; Engineering in Medicine and Biology 1999, p. 751, vol. 2.
Durmaz, S. et al. "Phase Separation during the Formation of Poly(acrylamide) Hydrogels" Polymer 41, 2000, pp. 5729-5735.
Gong, J.P. et al. "Friction of Polymer Gels and the Potential Application as Artificial Cartilage." SPIE, Mar. 1999, pp. 218-225, vol. 3669.
Guilherme, R. et al. "Hydrogels based on PAAm network with PNIPAAm included: hydrophilic-hydrophobic transition measured by the partition of Organe II and Methylene Blue in Water." Polymer 44, 2003, pp. 4213-4219.
Hassan, C.M. et al. "Modeling of Crystal Dissolution of Poly(vinyl alcohol) gels produced by freezing/thawing processes." Polymer 41, 2000, pp. 6729-6739.
Hassan, C.M. et al. "Structure and Morphology of Freeze/Thawed PVA Hydrogels," Macromolecules, 2000, pp. 2472-2479, vol. 33, No. 7.
Hickey, A.S. et al. "Solute Diffusion in Poly(vinyl) alcohol/poly(acrylic) acid composite membranes prepared by freezing/thawing techniques." J. Memb. Sci. 107, 1995, pp. 229-237.
Kobayashi, M. et al. "Development of an Artificial Meniscus Using Polyvinyl alcohol-hydrogel for early return to, and continuance of, athletic life in sportspersons with severe meniscus injury." Abstract only, The Knee 10, 2003, p. 53.
Kobayashi, M. et al. "Preliminary Study of Polyvinylalcohol-hydrogel (PVA-H) artificial meniscus." Biomaterials 24, 2003, pp. 639-647.
Lester, C.L. et al. "Physical Properties of Hydrogels Synthesized from Lyotropic Liquid Crystalline Templates" Chem. Mater. 15, 2003, pp. 3376-3384.
Mano, V. et al. "Blends Composed of Poly(N-Isopropylacrylamide) and an Ethylene/Vinyl Alcohol Copolymer: Thermal and Morphological Studies" J. App. Polymer Sci., 2004, pp. 501-505.

Park, J.H. et al. "Hydrogels based on Poly(ethylene oxide) and poly(tetramethylene oxide) or poly)dimethyl siloxane). III. In vivo Biocompatability and Biostability." J. Biomed. Mater. Res. 64A, 2003, pp. 309-319.

Schmedlen, R.H. et al. "Photocrosslinkable polyvinyl alcohol hydrogels that can be modified with cell adhesion peptides for use in tissue engineering." Biomaterials, 23, 2002, pp. 4325-4332.

Suggs, L.J. et al. "In vitro Cytotoxicity and in Vivo Biocompatability of Poly(propylene fumurate-co-ethylene glycol) hydrogels." J. Biomed. Mater. Res., 1999, pp. 22-32, vol. 46.

Thomas, J.D. "Novel Associated PVA/PVDP Hydrogels for Nucleuc Pulposus Replacement." Thesis, Master of Science in Material Engineering Degree, Drexel University, Sep. 2001.

Ushio, K. et al "Attachment of Artificial Cartilage to Underlying Bone." J. Biomed. Mater. Res. Part B: Appl. Biomater, 2004, pp. 59-68.

Ushio, K. et al. "Partial Hemiarthroplasty for the treatment of Osteonecrosis of the Femoral Head: An Experimental Study in the Dog." J. Bone Joint Surg., 2003, pp. 922-930, vol. 85B.

Zhang, X. et al. "Synthesis and Characterization of Partially Biodegradable, Temperature and pH Sensitive Dex-MA/PNIPAAm Hydrogels." Biomat., 25, 2004, pp. 4719-4730.

"Lecture 7: Hydrogel Biomaterials: Structure and Physical Chemistry," Spring 2003, 8 pages.

ISR/WO for PCT/US2006/006356 dated Jun. 22, 2006, 9 pages.

Bray, J.C. et al. "Poly(vinyl Alcoohol) Hydrogels: Formation by Eelctron Beam Irradiation of Aqueous Solutions and Subsequent Crystallization." J. Applied Polymer Sci., vol. 17, pp. 3779-3794, 1973.

Bray, J.C. et al. "Poly(vinyl Alcohol) Hydrogels for Synthetic Articular Cartilage Material," Biomed. Mater. Res., vol. 7, pp. 431-443, 1973.

Kawanishi, K. Thermodynamic Consideration of the Sol-Gel Transition in Polymer Solutions. 35th Annual Meeting of the Society of Polymer Science, Japan 1986.

Lozinsky, V.I. et al. "Study of Cryostructures of Polymer Systems, XIV. Poly(vinyl alchohol) Cryogels: Apparent Yield of Freeze-Thaw Induced Gelation of Concentrated Aqueous Solutions of the Polymer." J. Applied Polymer Sci., vol. 77, 1822,1831 (2000).

Lozinsky, V.I. et al. "Study of Cryostructuration of Polymer Systems, XVII. Poly(vinyl alcohol) Cryogels: Dynamics of the Cryotropic Gel Formation." J. Appl. Polymer Sci., vol. 77, 2017-2023 (2000).

Lozinsky, V.I. et al. "Swelling Behavior of poly (vinyl alcohol) cryogels employed as matrices for cell immobilization." Enzyme Microb. Technol., vol. 18.

Peppas et al. "Reinforced Uncrosslinkable Poly (vinyl alcohol) gels produced by cyclic freezing-thawing processes: A Short Review." J. Controlled Release, 16 (1991), 305-310.

Mondino, A.V. et al. "Physical properties of gamma irradiated poly (vinyl alcohol) hydrogel preparations" Radiation Physics and chemistry, 55, p. 723,726 (1999).

Urushizaki, F. Swelling and Mechanical Properties of Poly (vinyl alcohol) Hydrogels. Intl. J. Pharma., 58, 135-142, 1990.

Lozinsky, V.I. "On the Possibility of Mechanodestruction of Poly (vinyl Alcohol) Molecules under Moderate Freezing of its Concentrated Water Solutions." Polymer Bulletin, 15, p. 333-340 (1986).

Yokoyama, F. "Morphology and Structure of Highly Elastic Poly (vinyl alcohol) Hydrogel Prepared by Repeated Freezing-and-Melting" Colloid & Polymer Sci. 264, 595-601 (1986).

Covert, R.J. et al. "Friction and Wear Testing of a New Biomaterial for Use as an Articular Cartilage Substitute," BED 50 (2001), 355-356, Bioengineering Conference, ASME 2001.

Ding, Mei Yee. Characterisation of Polyvinyl Alcohol Hydrogels, 2003. Undergraduate Chemical Engineering Thesis, University of Queensland, Brisbane QLD 4072, Australia.

Jaguar-Grodzinski, J. "Biomedical Application of Functional Polymers." Reactive and Functional Polymers 39 (1999) 99-138.

Ulanski, P. et al. "OH-Radical induced crosslinking and strand breakage of poly (vinyl alcohol) in aqueous solution in the absence and presence of oxygen. A pulse radiolysis and product study" Macromol. Chem. Phys. 195, p. 1443-14461 (1994).

T. Noguchi et al., Poly(vinyl Alcohol) Hydrogel as an Artificial Articular Cartilage: Evaluation of Biocompatibility; Journal of Applied Biomaterials, vol. 2, 101-107 (1991), John Wesley & Sons, Inc. .

International Union of Pure and Applied Chemistry (IUPAC), Glossary of Basic Terms in Polymer Science; Pure Appl. Chem. 68, 2287-2311 (1996), Great Britain.

D. A. Babb et al., Perfluorocyclobutane Aromatic Ether Polymers. III. Synthesis and Thermal Stability of a Thermoset Polymer Containing Triphenylphosphine Oxide; Journal of Applied Polymer Science, vol. 69, 2005-2012 (1998), John Wiley & Sons, Inc.

Peppas et al., Physicochemical Foundations and Structural Design of Hydrogels in Medicine and Biology; Annu. Rev. Biomed Eng, vol. 2, 9-29 (2000).

Hassan et al., Structure and Applications of Poly(vinyl Alcohol) Hydrogels Produced by Conventional Crosslinking or by Freezing/Thawing Methods; Advances in Polymer Science, vol. 153, 37-65 (2000), Springer-Verlag Berlin Heidelberg.

Taguchi. Chemistry Letters, 711-712 (1998).

Lu et al. Journal of Controlled Release, 57, 291-300 (1999).

West et al. Reactive Polymers, 139-147 (1995).

Green et al. Organic Chemistry Principles and Industrial Practice. Wiley VCH, 2003.

Mondino et al. Rad. Chem. and Phys. 55, 723-726 (1999).

Jagur-Grodzinski in Reactive and Functional Polymers, 39, 99-139 (1999).

Tripathy et al. "Novel Flocculating Agent Based on Sodium Alginate and Acrylamide." European Polymer Journal. 35, 2057-2072 (1999).

Haralabakopoulus et al. J. Appl. Poly. Sci., 69, 1885-1890 (1998).

Hickey et al., "Mesh Size and Diffusive Characteristics of Semicrystalline . . . ", Journal of Membrane Science 107 (1995) pp. 229-237.

Bryant, Stephanie et al, "Phtocrosslinkable Poly(ethylene oxide) and Poly (vinyl Alcohol) Hydrogels for Tissue Engineering Cartilage", First Joint BMES/EMBS Conference, p. 751, Oct. 1999 Atlanta Georgia.

Yamaura, Kazuo, et al, "Properties of Gels Obtained by Freezing/Thawing of Poly(vinyl Alcohol)/Water/Dimethyl Sulfoxide Solutions," Journal of Applied Polymer Science, vol. 37 pp. 2709-2718, 1989.

Yokoyama, F., et al, "Morphology & Structure of highly elastic poly (vinyl alcohol) hydrogel prepared by repeated freezing-and-melting," Colloid & Polymer Science, vol. 264, pp. 595-601, 1986.

EP Search Report for EP Application No. 050010009.9-2115 dated Mar. 1, 2005.

EPO Invitation to Pay additional fees and Annex to Search Report for PCT/US2006/046725 dated Apr. 22, 2008, 8 pages.

Search Report and Written Opinion for PCT/US2008/071435 dated Feb. 5, 2009.

Preliminary Report on Patentability & Written Opinion for PCT/US2008/086817 dated Jul. 6, 2010.

Search Report and Written Opinion for PCT/US2008/083213 dated May 8, 2009.

Preliminary Report on Patentability & Written Opinion for PCT/US2008/071539 dated Mar. 2, 2010.

Preliminary report on Patentability & Written Opinion for PCT/US2006/006356 dated Aug. 28, 2007.

* cited by examiner

HYDROGELS WITH GRADIENT

TECHNICAL FIELD

The present invention relates to hydrogel articles having a multi-layered structure and exhibiting a gradient in polymer molecular weight that may be suitable for use in biomedical or other applications.

BACKGROUND

Hydrogels are water-swellable or water-swollen materials whose structure is defined by a crosslinked network of hydrophilic homopolymers or copolymers. The hydrophilic homopolymers or copolymers can be water-soluble in free form, but in a hydrogel, they are rendered insoluble due to the presence of covalent, ionic, and/or physical crosslinks. In the case of physical crosslinking, the linkages can take the form of entanglements, crystallites, or hydrogen-bonded structures. The crosslinks in a hydrogel provide structure and physical integrity to the network.

One desirable feature of hydrogels for biomedical applications is that the hydrogels are very absorbent. Hydrogels can have a moisture content of upwards of 70% in many cases. In contrast, polyurethane hydrogels commonly employed in implantable devices are generally characterized by low moisture content, on the order of a few percent.

Hydrogels can attain a wide variety of mechanical properties. In general, hydrogels are observed to be pliable or rubbery, with a lubricious surface. Hydrogels are generally characterized by a low coefficient of friction owing to the water content and water-release properties at the surface. However, problems commonly associated with hydrogels that possess desirable absorbent properties include low mechanical strength and low shear strength. Devices made from PVA hydrogels have been observed to fail due to wear, such as by tearing, abrasion, or shredding. Thus, achieving improved mechanical strength and other physical properties for implantable articles made from hydrophilic polymers is desired.

SUMMARY OF THE INVENTION

The present invention provides a hydrogel article having a multi-layered structure and having a first and an opposing second surface. Each layer of the multi-layered structure is formed from a polymer having a different polymer molecular weight such that the multi-layered structure forms an increasing gradient in polymer molecular weight and strength from the first surface to the second surface. The gradient in polymer molecular weight also results in a decreasing gradient in porosity and water concentration from the first surface to the second surface.

The present invention also provides a method of producing a hydrogel article having a multi-layered structure that exhibits a gradient in polymer molecular weight and comprises at least a first constituent and a second constituent. The method comprises forming a first layer comprising the first constituent, which is a polymer having a first molecular weight. The first layer is then contacted with the second constituent, which is a polymer having a second molecular weight different than the first molecular weight, and forms a second layer of the multi-layered structure. The resulting hydrogel article exhibits a gradient of polymer molecular weight and the gradient of polymer molecular weight results in a gradient of strength, water concentration, and porosity.

DETAILED DESCRIPTION

Figure 1:
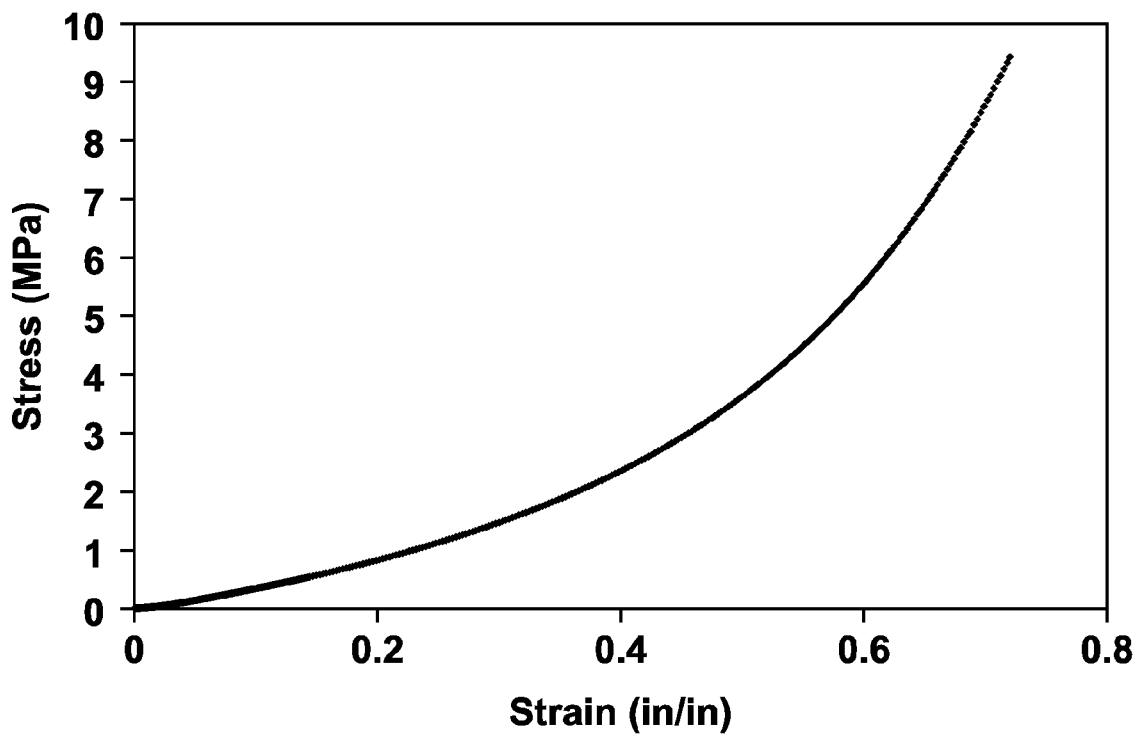
FIG. 1 shows compressive stress-strain data for an injection molded PVA hydrogel in unconfined compression.

The present invention provides for a hydrogel article comprising a multi-layered structure where each layer of the multi-layered structure comprises a polymer having a molecular weight such that the multi-layered structure forms a gradient in polymer molecular weight. In one embodiment, the layers of the multi-layered structure are formed from the same polymer but vary in polymer molecular weight. Furthermore, the gradient in polymer molecular weight results in a gradient in strength, porosity, and water concentration.

The hydrogel article also has a first and a second surface, the multi-layered structure defined therebetween with the first surface exhibiting a lower polymer molecular weight, a higher water concentration, a higher porosity, and a lower strength than the second surface. The hydrogel article of the present invention provides the combination of both a strong surface, which may be used as a bone-contacting surface, and a lubricious surface, which may be used as an articulating surface.

As used in this specification, the term "hydrogel" indicates that the article is able to absorb and retain water within a network of polymers, and does not imply that a change in volume of the article necessarily occurs upon hydration.

In one embodiment, the multi-layered structure of the hydrogel article exhibits a continuous gradient in polymer molecular weight. In another embodiment, the multi-layered structure of the hydrogel article exhibits discrete layers in polymer molecular weight. In another embodiment, the multi-layered structure of the hydrogel article exhibits a combination of continuous gradient and discrete layers in polymer molecular weight. Discrete layers represent an abrupt change in polymer molecular weight at the layer boundaries whereas a continuous gradient represents a gradual change in polymer molecular weight at the layer boundaries. In one embodiment, discrete layers can be represented as a substantially "stair-step" graph when plotted as a function of distance across the gradient versus polymer molecular weight whereas a continuous gradient would be represented as a substantially smooth line.

The present invention also provides a method of producing a hydrogel article having at least a first constituent and a second constituent and having a multi-layered structure that exhibits a gradient in polymer molecular weight. The method comprises forming a first layer of the multi-layered structure from the first constituent, which is a polymer having a first molecular weight. The first layer is then contacted with a second constituent, which is a polymer having a second molecular weight. The second constituent forms a second layer of the multi-layered structure of the hydrogel article. In one embodiment, the first and second constituents are the same polymer but vary in polymer molecular weight. Additional layers of the multi-layered structure can be formed by contacting the second layer with a third constituent having a third polymer molecular weight. The process of contacting the previously formed layer with a subsequent constituent having a different polymer molecular weight can be repeated as many times as desired. Although the inventive hydrogel article and method of making the hydrogel article is understood to describe a multi-layered structure having at least two layers, for clarity sake, the descriptions will be limited to the first and second layers. However, it should be understood that the descriptions of the first and second layers can be applied to any or all subsequent layers, e.g. layers three, four, five, etc. In one embodiment, the polymer molecular weight of the constituents, and thus the layers that are formed from the constituents, increases with each subsequent cycle of forming a layer and contacting the layer with a constituent. In another embodiment, the polymer molecular weight of the constituents, and thus the layers that are formed from the constituents, decreases with each subsequent cycle of forming a layer and contacting the layer with a constituent.

The result of the cycles of forming a layer and then contacting the layer with another constituent is a hydrogel article having a multi-layered structure exhibiting a gradient of polymer molecular weight. Polymer molecular weight is directly proportional to strength and inversely proportional to porosity and associated water concentration. The inverse relationship between polymer molecular weight and water concentration is believed to be a result of the increased molecular size and chain entanglement of the larger polymeric molecules. Additionally, increased polymer molecular weight also leads to higher resistance to creep, which is a time-dependent strain that occurs under the application of stress. Thus, a gradient in polymer molecular weight also results in a gradient in strength, porosity, and water concentration.

In one embodiment, the multi-layered structure is formed by contacting the first layer with a second constituent while the first layer is either in a flowable state, a semi-solid state, or a solid state. In one embodiment, the multi-layered structure is formed by contacting the first layer with a second constituent while the second constituent is either in a flowable state, a semi-solid state, or a solid state. The first layer is contacted with the second constituent by a variety of means including injection molding, solution casting, compression molding, extrusion, centrifugation, ultracentrifugation, or spin coating. In various embodiments, there is some degree of mixing of the first and second constituents at the boundary between the first and second layers. For instance, in embodiments where both the first layer, and therefore the first constituent, and the second constituent are in a flowable state, mixing between the two constituents may occur. Mixing between the first and second constituents results in a gradual change in polymer molecular weight comprising the polymer molecular weight gradient. Conversely, in embodiments where mixing between the first and second constituents does not occur, discrete layers of polymer molecular weight are created and thus, an abrupt change in polymer molecular weight comprising the polymer molecular weight gradient is created. For example, when the first layer and/or the second constituent are in a solid state, little to no mixing between the two constituents occurs. In some embodiments, the multi-layered structure of the hydrogel article contains a combination of discrete and gradual changes in polymer molecular weight at the layer boundaries. The boundaries are bounded by diffusion of molecular weights throughout the construct, but may be bound by other methods including reactive groups, gamma cross linking, cross linking agents, cyanoacrylates, or UV irradiation.

The inventive method also includes shaping and/or molding the hydrogel article comprising a polymer molecular weight gradient. In one embodiment, the hydrogel article formed by the inventive method is shaped and/or molded for use in an orthopedic procedure.

In one embodiment, the hydrogel article is an articulating surface replacement. In one embodiment, the articulating surface replacement has a first and a second surface and at least two layers forming the multi-layered structure. In one embodiment, the first surface of the articulating surface replacement is a bone-contacting surface and the second surface is an articulating surface and the gradient in polymer molecular weight ranges from a higher polymer molecular weight at the bone-contacting surface to a lower polymer molecular weight at the articulating surface. As described above, the higher polymer molecular weight results in lower water concentration and porosity and the lower polymer molecular weight results in higher water concentration and porosity. Additionally, the higher polymer molecular weight correlates with increased strength and the lower polymer molecular weight correlates with decreased strength. Thus, in an embodiment where the first surface of the articulating surface replacement is a bone-contacting surface and has a higher polymer molecular weight and the second surface is an articulating surface and has a lower polymer molecular weight, the first surface exhibits increased strength while the second surface exhibits increased water concentration. The increase in water concentration exhibited by the lower polymer molecular weight increases the lubricity of the material. In such an embodiment, the hydrogel article forming the articulating surface replacement provides desired strength at the bone-contacting surface and also desired lubricity at the articulating surface.

In one embodiment, the constituents that form the hydrogel article of the present invention are hydrophilic polymers. The hydrophilic polymers may be polyvinyl alcohol, for example, that vary in polymer molecular weight. By way of illustration only, other suitable hydrophilic polymers include polyhydroxyethyl methacrylate, polyvinyl pyrrolidone, polyacrylamide, polyacrylic acid, hydrolyzed polyacrylonitrile, polyethyleneimine, ethoxylated polyethyleneimine, polyallylamine, polyglycols as well as blends or mixtures of any of these hydrophilic polymers.

For example, in embodiments where the hydrophilic polymer is PVA, the constituents used to form the multi-layered structure may have polymer molecular weights selected from about 89 kilodaltons (kDa), about 130 kDa, about 186 kDa, and/or about 250 kDa. In certain embodiments, PVA molecular weights of about 89 kDa, about 130 kDa, about 186 kDa, and about 250 kDa corresponds to water contents of about 62.1%, 57.8%, 57.0%, and 56.1%, respectively.

In some embodiments of the present invention, the hydrophilic polymer may be a hydrogel blend including PVA and a second polymer having, for instance, hydrophobic recurring units and hydrophilic recurring units. For example, the second polymer of the hydrogel blend may be polyethylene-co-vinyl alcohol. As non-limiting examples, other suitable polymers include diol-terminated polyhexamethylene phthalate and polystyrene-co-allyl alcohol.

In certain embodiments of the invention, the hydrophilic polymer may be a copolymer. A copolymer derived from a hydrophobic monomer and a hydrophilic monomer may be suitable as the polymer, for example. One specific example of a suitable copolymer is polyethylene-co-vinyl alcohol, also known as "EVAL," "PEVAL" or "EVOH." Other copolymers having hydrophilic recurring units and hydrophobic recurring units that may be suitable include poly(ethylene-co-acrylic acid) and polyethylene-co-methacrylic acid. Further examples of suitable materials to be used in the hydrogel article can be found in U.S. patent application Ser. No. 11/614,389, incorporated by reference herein in its entirety.

The hydrogel article may also include additional polymers, or conventional additives such as plasticizers, components for inhibiting or reducing crack formation or propagation, components for inhibiting or reducing creep, or particulates or other additives for imparting radiopacity to the article. By way of example only, an additive for imparting radiopacity can include metal oxides, metal phosphates, and/or metal sulfates such as barium sulfate, barium titanate, zirconium oxide, ytterbium fluoride, barium phosphate, and ytterbium oxide.

The hydrogel article of the present invention can be used in a variety of applications, including orthopedic procedures, as known in the field. By way of example, the hydrogel article can be used to provide artificial articular cartilage. The hydrogel article can also be employed as artificial meniscus or articular bearing components. For example, the hydrogel article having the combination of properties described above, e.g. a mechanically strong surface and a lubricious surface, may be used as an implant or in a reparative procedure of the knee joint, shoulder, etc. The hydrogel article can also be employed in temporomandibular, proximal interphalangeal, metacarpophalangeal, metatarsalphalanx, hip capsule or other joint repair. The hydrogel article of the present invention can also be used to replace or rehabilitate the nucleus pulposus of an intervertebral disc.

Optionally, a layer, more than one layer, or the hydrogel article of the present invention may be subjected to one or more crosslinking steps. Crosslinking may be carried out after forming a layer, after forming a multi-layered structure, after molding or shaping the hydrogel article, or at any other suitable point during processing. In one embodiment, a boundary between two layers may be subjected to crosslinking. In one embodiment, crosslinking of the boundary between two layers results in increased adhesion between the layers. A variety of conventional approaches may be used to crosslink the composite material, including, physical crosslinking (e.g., freeze thaw method), photoinitiation, irradiation and chemical crosslinking.

EXAMPLES

The following examples illustrate the synthesis of PVA polymer hydrogels to be used in the multi-layered structure in one embodiment of the invention. The resulting hydrogels were subjected to mechanical analysis.

PVA hydrogels were produced from four different PVA polymer molecular weights: 89 k, 130 k, 186 k and 250 k g/mol. The 89 k, 130 k, and 186 k polymers were purchased from Sigma Aldrich (St. Louis Mo.), and the 250 k PVA was purchased from Vam & Poval Co., Ltd. (Japan). A Haake POLYLAB rheometer was used to compound PVA and dimethyl sulfoxide (DMSO)/water. Disks having a diameter of 50 mm and a thickness of 4 mm were injection molded from the compounded PVA polymers. Molded samples were initially solvent exchanged in isopropyl alcohol for 24 hours, followed by sequential 24-hour solvent exchanges in deionized water. Samples remained in water for a minimum of 48 hours to fully hydrate prior to testing.

Unconfined compression testing was performed in deionized water at room temperature using an Instron 3345 test frame. Test samples consisted of fully hydrated 13 mm diameter, 4 mm thick cylinders that were punched out from the injection molded disks. Samples were loaded at 0.05 in/min according to ASTM D695 and tangent modulus was calculated at 10% strain increments up to 70% strain.

Static creep testing was performed in deionized water at room temperature on a custom-built test system. Cylindrical hydrogel samples with 13 mm diameter and 4 mm thickness punched from injection molded disks were loaded to a constant stress level of approximately 1 MPa for 16 hours, followed by 8 hours recovery. Change in thickness of the samples was recorded over time. Creep strain was calculated as the percent change from initial thickness. Creep modulus was defined as stress applied divided by the creep strain.

A TA Instruments 2980 TGA was used to verify water content of the hydrogels. In a nitrogen environment, samples were heated at 10° C. per minute to 110° C., and then held isothermal for 45 minutes to drive off water. The weight percent water loss was determined from the resulting TGA curve and corresponded to the water content of the gel.

Figure 2:
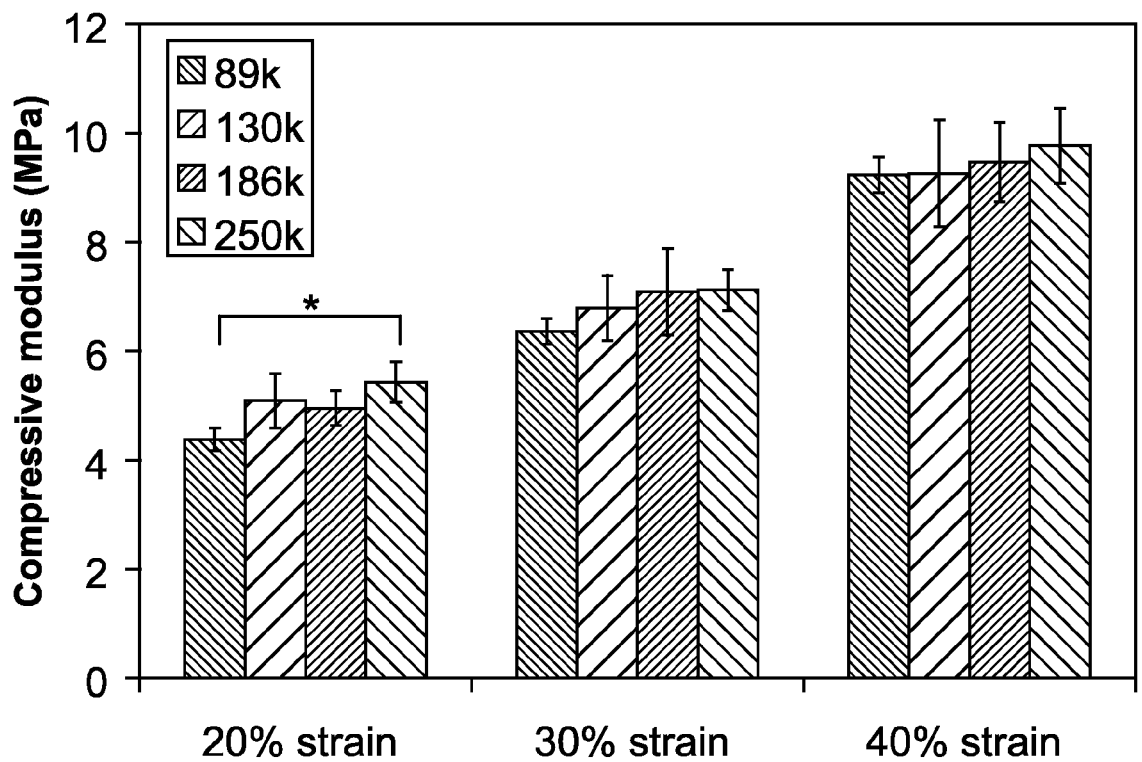
FIG. 2 shows compressive moduli of PVA hydrogels with different molecular weights.

A typical stress-strain data for an injection molded PVA hydrogel, e.g. 250 k g/mol PVA, is shown in FIG. 1. The stress-strain behavior is non-linear, with tangent modulus increasing rapidly with increasing strain level. Modulus was calculated by regression analysis of the compression data at percent strain of 20%, 30%, and 40% and is shown in FIG. 2. Asterisk indicated significant difference among the samples ($p<0.05$, statistical analysis by Design Expert). FIG. 2 shows a statistically significant trend for tangent modulus versus PVA molecular weight at 20% strain.

Figure 3:
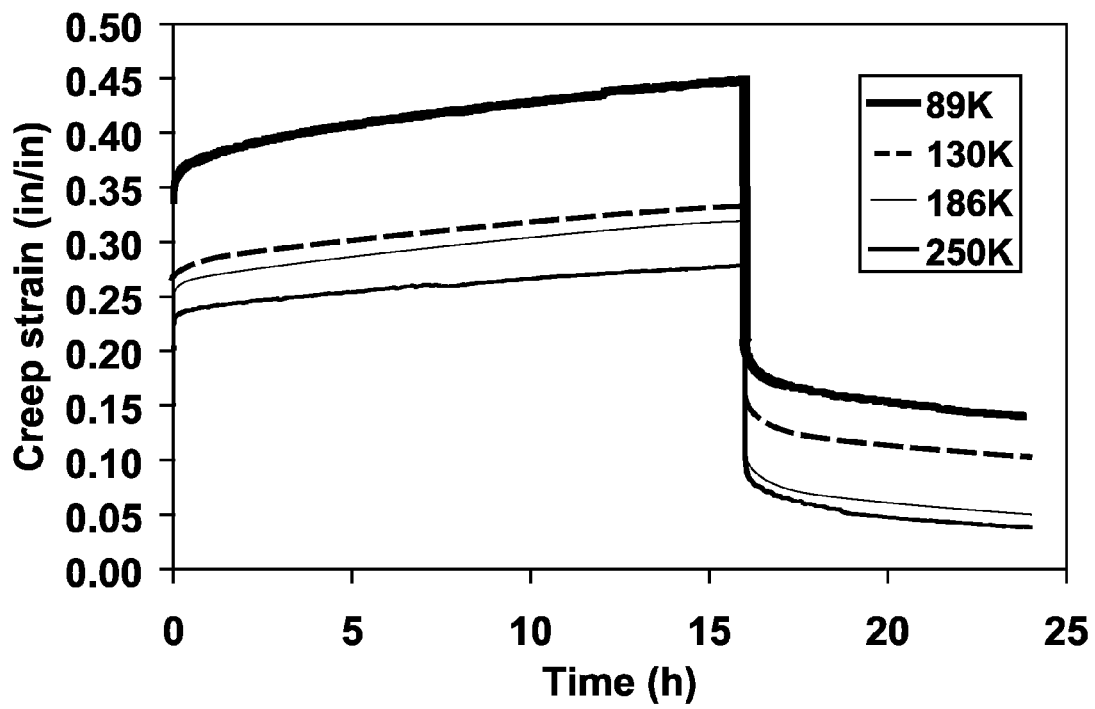
FIG. 3 shows the behavior of creep strain over time during creep test for an injection molded PVA hydrogel.
Figure 4:
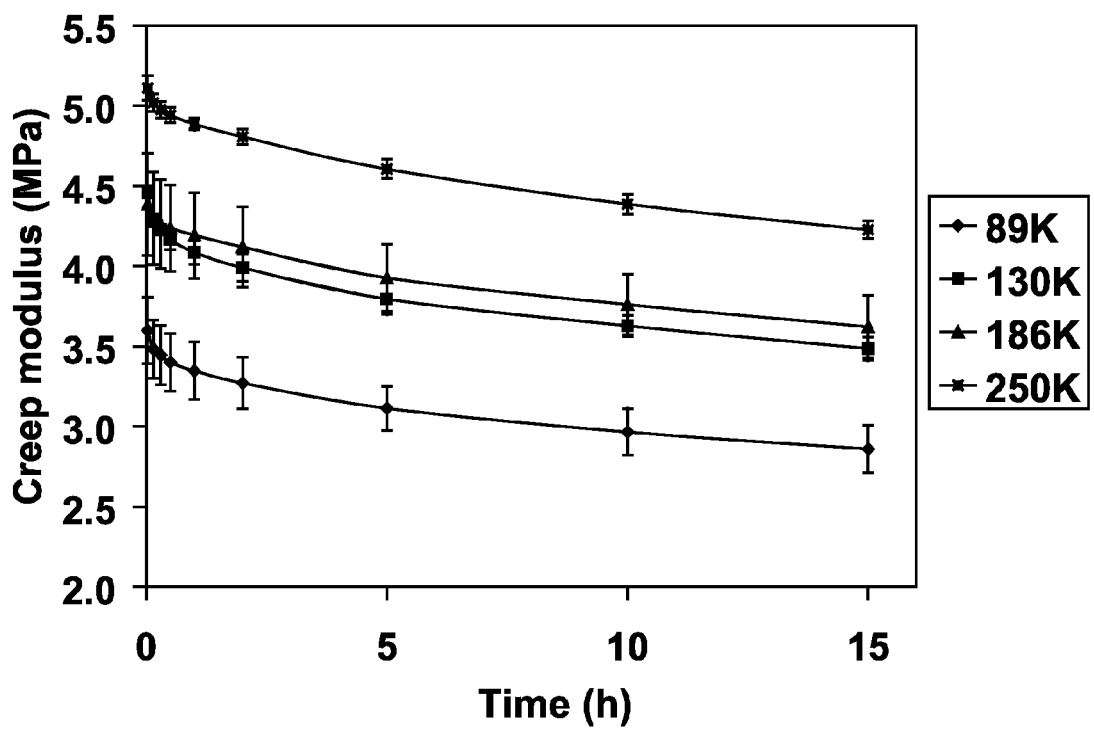
FIG. 4 shows creep modulus over time for PVA hydrogels of different molecular weights.

Hydrogels exhibited viscoelastic behavior under compressive creep load, as shown in FIG. 3. Test results showed that creep strain after 16 hours decreased with increasing PVA molecular weight. On unloading, all of the PVA hydrogels exhibited similar recovery trends, though final strain after 8 hours was lower for the higher molecular weight PVAs. FIG. 4 shows that creep modulus also showed a strong correlation with the molecular weight of PVA in the sample.

Because the process of molding the hydrogels utilizes dimethylsulfoxide as the solvent, the final water content of the hydrogels after solvent exchange is different than the solvent concentration at time of molding. Water concentration is determined as the percentage weight loss using a thermogravametric analysis instrument with a ramp of 10° C./min to 120° C., an isotherm for 45 minutes, followed by a 10° C./min ramp to 160° C. The final water content measured from fully hydrated, injection molded PVA components differed from the initial 54% solvent concentration for each molecular weight PVA at the compounding step (Table 1).

TABLE 1

| Water content of hydrogels. | | | | |
|---|---|---|---|---|
| | Molecular weight (k g/mol) | | | |
| | 89 | 130 | 186 | 250 |
| Water content (%) | 62.1 | 57.8 | 57.0 | 56.1 |

Results from the static unconfined compression and compressive creep experiments demonstrate that bulk polymer molecular weight affects the mechanical properties of injection molded PVA hydrogels.

The invention is further set forth in the claims listed below. This invention may take on various modifications and alterations without departing from the scope thereof. In describing embodiments of the invention, specific terminology is used for the sake of clarity. The invention, however, is not intended to be limited to the specific terms so selected, and it is to be understood that each term so selected includes all technical equivalents that operate similarly.

What is claimed is:

1. A hydrogel article comprising a multi-layered structure and having a first surface and an opposing second surface, wherein each layer of the multi-layered structure comprises a polymer having a different polymer molecular weight such that the multi-layered structure forms an increasing gradient in polymer molecular weight and strength from the first surface to the second surface, and wherein the gradient in polymer molecular weight results in a decreasing gradient in porosity and water concentration from the first surface to the second surface.

2. The hydrogel article of claim 1 wherein each layer of the multi-layered structure is formed from the same polymer but each layer of the multi-layered structure varies in polymer molecular weight.

3. The hydrogel article of claim 1 wherein the multi-layered structure exhibits a continuously increasing gradient of polymer molecular weight.

4. The hydrogel article of claim 1 wherein the multi-layered structure exhibits discrete layers of different polymer molecular weight.

5. A method of producing a hydrogel article having a multi-layered structure that exhibits a gradient in polymer molecular weight and comprises at least a first constituent and a second constituent, the method comprising
    forming a first layer comprising the first constituent, wherein the first constituent is a polymer having a first molecular weight, and
    contacting the first layer with the second constituent having a second molecular weight different than the first molecular weight, wherein the second constituent forms a second layer of the multi-layered structure, and whereby a hydrogel article is formed exhibiting a gradient of polymer molecular weight, and whereby the gradient of polymer molecular weight results in a gradient of strength, water concentration, and porosity.

6. The method of claim 5 wherein the first layer is either in a flowable state, a semi-solid state, or a solid state when the first layer is contacted with the second constituent.

7. The method of claim 5 wherein the second constituent is either in a flowable state, a semi-solid state, or a solid state when the first layer is contacted with the second constituent.

8. The method of claim 5 wherein the first layer is contacted by the second constituent by injection molding.

9. The method of claim 5 further comprising contacting the second or a subsequent layer of the multi-layered structure with a third or a subsequent constituent having a different polymer molecular weight such that a hydrogel article having a multi-layered structure exhibiting a gradient in polymer molecular weights is formed.

10. The method of claim 5 further comprising shaping and/or molding the hydrogel article.

11. The method of claim 5 wherein the resultant multi-layered structure of the hydrogel article exhibits discrete layers of polymer molecular weight, or a continuous gradient of polymer molecular weights, or a combination thereof.

12. The method of claim 5 wherein the hydrogel article is used as an articulating surface replacement having a first and a second surface, wherein the first surface is a bone-contacting surface and the second surface is an articulating surface, and wherein the gradient in polymer molecular weight ranges from a higher polymer molecular weight and strength at the bone-contacting surface to a lower polymer molecular weight and strength at the articulating surface, and wherein the higher polymer molecular weight results in lower water concentration and porosity at the bone-contacting surface and the lower polymer molecular weight results in higher water concentration and porosity at the articulating surface.

* * * * *